(12) United States Patent  (10) Patent No.: US 7,424,145 B2
Horie et al.  (45) Date of Patent: Sep. 9, 2008

(54) DEVICE AND METHOD FOR INSPECTING PHOTOMASKS AND PRODUCTS FABRICATED USING THE SAME

(75) Inventors: Tsutomu Horie, Kawasaki (JP); Kazutoshi Ohta, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 614 days.

(21) Appl. No.: 10/607,039

(22) Filed: Jun. 27, 2003

(65) Prior Publication Data
US 2004/0008880 A1 Jan. 15, 2004

(30) Foreign Application Priority Data
Jul. 9, 2002 (JP) .............................. 2002-199595

(51) Int. Cl.
G06K 9/00 (2006.01)
G06F 9/45 (2006.01)
(52) U.S. Cl. ......................................... 382/147; 716/5
(58) Field of Classification Search ................ 382/144, 382/141, 147; 716/5
See application file for complete search history.

(56) References Cited

U.S. PATENT DOCUMENTS

| | | | |
|---|---|---|---|
| 6,507,944 B1 * | 1/2003 | Kikuchi et al. ................ | 716/21 |
| 6,598,211 B2 * | 7/2003 | Zachariah et al. .............. | 716/4 |
| 6,617,083 B2 * | 9/2003 | Usui et al. ..................... | 430/5 |
| 6,711,733 B2 * | 3/2004 | Noda ........................... | 716/19 |
| 6,721,695 B1 * | 4/2004 | Chen et al. ..................... | 703/7 |
| 6,865,288 B1 * | 3/2005 | Shishido et al. ............. | 382/145 |
| 2002/0027653 A1 * | 3/2002 | Shibata et al. ........... | 356/237.3 |

OTHER PUBLICATIONS

English Language Abstract JP No. 03-170002A dated Jul. 23, 1991.
English Language Abstract JP No. 58-223328A dated Dec. 24, 1983.
English Language Abstract JP No. 2000-146857A dated May 26, 2000.
Japanese Office Action issued on Apr. 3, 2007 in corresponding Japanese Application No. 2002-199595 discussing Japanese Reference No. 2000-146857, the abstract of which is of record.

* cited by examiner

*Primary Examiner*—Bhavesh Mehta
*Assistant Examiner*—Hadi Akhavannik
(74) *Attorney, Agent, or Firm*—Staas & Halsey LLP

(57) ABSTRACT

An inspection device for photomasks and products fabricated using the same, capable of reducing the time from inspection to repair. A reference data generator generates reference data that is based on design data and includes sensitivity class codes that differentiate designated pattern functions such as signal lines and power supply lines by means of inspection sensitivity. Then an inspection sensitivity setter allocates the desired inspection sensitivity for each sensitivity class code. An image acquiring unit photographs a subject of inspection (e.g., photomask or wafer), and a comparator detects a defect by comparing the photographed image with the reference data. When a defect is found, a reference data extractor extracts the region of the reference data that corresponds to the defect location. A defect registration determinator refers to the sensitivity class codes for the region and determines whether to register the defect. This reduces the number of defects that are registered.

11 Claims, 12 Drawing Sheets

DEVICE AND METHOD FOR INSPECTING PHOTOMASKS AND PRODUCTS FABRICATED USING THE SAME

CROSS-REFERENCE TO RELATED APPLICATIONS

This application is based upon and claims the benefits of priority from the prior Japanese Patent Application No. 2002-199595, filed on Jul. 9, 2002, the entire contents of which are incorporated herein by reference.

BACKGROUND OF THE INVENTION

1. Field of the Invention

The present invention relates to an inspection device and method, and particularly to a device and method for inspecting photomasks and products fabricated using the same.

2. Description of the Related Art

As part of the advancing miniaturization of large-scale integrated circuits (LSI), recently the degree of precision is increasing not only for patterned wafers, but also for the photomasks such as reticles that are used when manufacturing LSI chips. This leads to a demand for a more sensitive inspection device that can detect smaller defects on a photomask or fabricated wafer.

FIG. 12 is a block diagram that shows a conventional inspection device. The inspection device 100 compares the actual pattern of, for example, a photomask 110 with its source design data that was used when drawing the actual pattern (the process known as die-to-database inspection). In this case, the inspection device 100 is formed from the following elements: (a) a reference data generator 101 that, based on design data, generates reference data that is to be used for the inspection; (b) an inspection condition setter 102 for setting inspection conditions; (c) an image acquiring unit 103 for acquiring as image data the actual pattern of the photomask 110 that is to be inspected; (d) image converters 104 and 105 for converting the reference data and the acquired pattern data into images for the purpose of comparison; (e) a comparator 106 for comparing the reference data with the data to be inspected and detecting defects; (f) a defect memory 107 for recording the detected defects; and (g) an inspection/drive controller 108 for driving a stage 108a on which the photomask 110 is mounted as the subject of the inspection, and for controlling the entire inspection device 100.

The inspection device 100 operates as follows. When design data is supplied, the reference data generator 101 produces reference data that is in a format suitable for inspection. Then, inspection begins after the inspection condition setter 102 inputs such settings as inspection sensitivity. First, the reference data is converted into an image by the image converter 104 and input to the comparator 106. At the same time, the actual pattern of the photomask 110, which has been acquired by the image acquiring unit 103, is sent to the image converter 105 as the data to be inspected, where it is converted into an image and input to the comparator 106. The comparator 106 refers to the inspection sensitivity that was set by the inspection condition setter 102, compares the two images, and determines whether there are any defects in the photomask image. Next, in the case that defects are detected, they are recorded in the defect memory 107. The inspection/drive controller 108 inspects the entire area of the photomask 110 by scanning the stage 108a. In this way, the conventional inspection device 100 compares the actual pattern data with the reference data and detects differences as defects.

However, the conventional inspection device 100 has a problem in that when sensitivity is raised, it mistakenly generates a false defect even if that location is not a defect. Also, depending on the location of the photomask defect, some defects do not affect performance or characteristics of the products fabricated with the photomask. Such labor as the repair of defects that are not problematic is in itself a problem.

SUMMARY OF THE INVENTION

In view of the foregoing, it is an object of the present invention to provide an inspection device capable of reducing the time from inspection to repair.

It is another object of the present invention to provide an inspection method capable of reducing the time from inspection to repair.

To accomplish the first object, according to the present invention, there is provided an inspection device that identifies defects on a subject of inspection including photomasks or products fabricated using photomasks. This inspection device has the following elements: (a) a reference data generator that generates reference data that is based on design data and includes sensitivity class codes that are used to differentiate designated pattern functions by means of inspection sensitivity; (b) an inspection sensitivity setter that allocates desired inspection sensitivities to the sensitivity class codes; (c) an image acquiring unit that photographs the subject of the inspection and generates the data to be inspected; (d) a comparator that compares the data to be inspected with the reference data and detects a defect; (e) a reference data extractor that extracts a region of the reference data that corresponds to where the detected defect exists; (f) a defect registration determinator that refers to the sensitivity class codes in the region and determines whether to register the defect; and (g) a defect memory that records the defect for which registration has been determined.

Additionally to accomplish the second object stated above, according to the present invention, there is provided an inspection method to identify defects on a subject of inspection including photomasks or products fabricated using photomasks. This inspection method (a) generates reference data that is based on design data and includes sensitivity class codes that are used to differentiate designated pattern functions by means of inspection sensitivity; (b) allocates desired inspection sensitivities to the sensitivity class codes; (c) photographs the subject of the inspection and generates data to be inspected; (d) compares the data to be inspected with the reference data and detects a defect; (e) extracts a region of the reference data that corresponds to where the detected defect exists; (f) determines whether to register the defect, by referencing the sensitivity class codes of the pattern functions in the extracted region; and (g) records the defect for which registration has been determined.

The above and other objects, features and advantages of the present invention will become apparent from the following description when taken in conjunction with the accompanying drawings which illustrate preferred embodiments of the present invention by way of example.

DESCRIPTION OF THE PREFERRED EMBODIMENTS

Preferred embodiments of the present invention will be described below with reference to the accompanying drawings.

Figure 1:
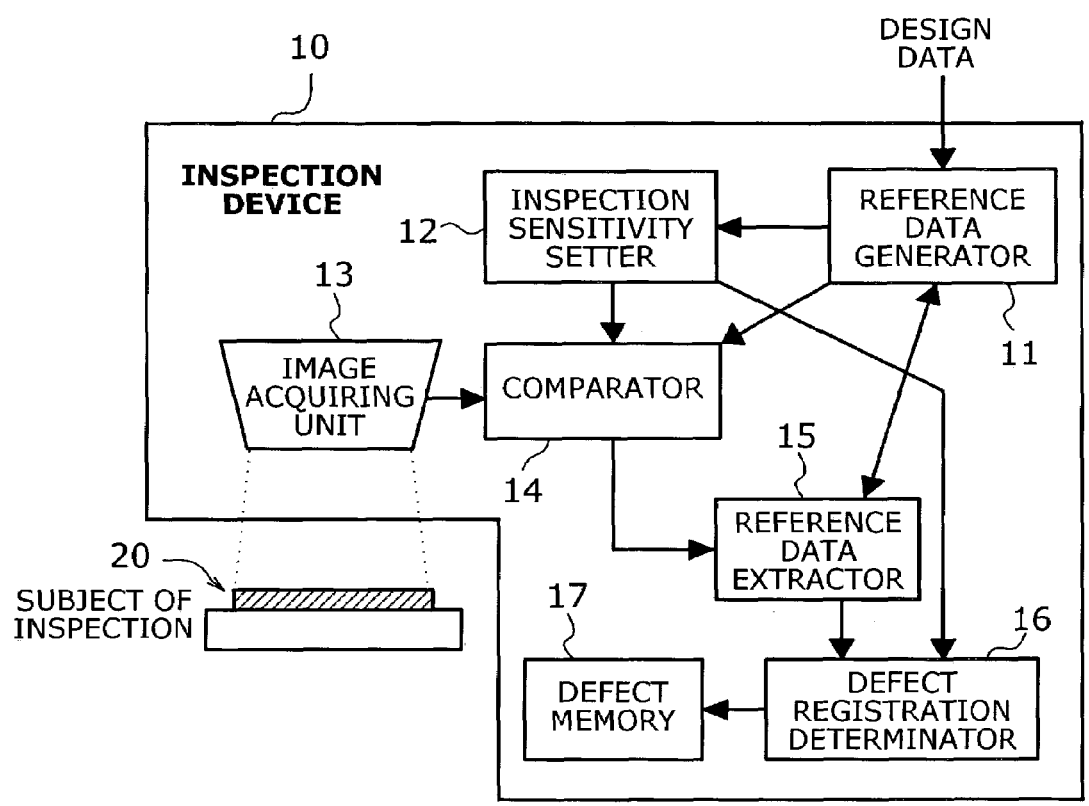
FIG. 1 is a block diagram that shows the concept of an inspection device according to the invention.

FIG. 1 is a block diagram that shows the concept of an inspection device according to the invention. This inspection device 10 identifies defects on the subject of inspection including photomasks or products fabricated using photomasks. Photomasks include reticles used with lithography equipment (known as steppers) for producing semiconductor chips and other microelectronic devices. The products that can be tested with the proposed inspection device 10 include wafers, substrates, circuit boards, and other devices on which patterns are formed. All those things can be the subject of the inspection according to the present invention, although in actual implementations inspection devices may be designed for a particular type of photomasks or products.

According to the present invention, the inspection device 10 is made up of: (a) a reference data generator 11 that generates reference data that is based on design data and includes sensitivity class codes that are used to differentiate pattern functions by means of inspection sensitivity; (b) an inspection sensitivity setter 12 that allocates desired inspection sensitivities to the sensitivity class codes; (c) an image acquiring unit 13 that photographs a subject 20 and generates data to be inspected; (d) a comparator 14 that compares the data to be inspected with the reference data and detects a defect; (e) a reference data extractor 15 that extracts a region of the reference data that corresponds to where the detected defect exists; (f) a defect registration determinator 16 that refers to the extracted reference data's sensitivity class code and determines whether to register the defect; and (g) a defect memory 17 that records a defect.

The reference data generator 11 generates reference data that is based on design data and to which it appends a sensitivity class code for each designated pattern function. The term "pattern function" refers to the specific function (such as signal lines or power lines) that each pattern feature is supposed to serve. Sensitivity class codes are used to differentiate pattern functions by means of inspection sensitivity. For example, sensitivity class code "1" is assigned to signal lines, and "2" to power lines. In addition to numbers, characters or symbols or any combination of them can be used as sensitivity class codes to differentiate pattern functions. The inspection sensitivity setter 12 allocates the desired inspection sensitivities to the sensitivity class codes, for example, inspection sensitivity 0.5 µm to the pattern function having sensitivity class code "1," and 1.0 µm to the pattern function having sensitivity class code "2." As will be described later, the values of inspection sensitivity denote, for example, the minimum size of pattern defects that will be detected if present. In other words, each inspection sensitivity value gives a threshold for defect detection.

The image acquiring unit 13 photographs the subject 20 of the inspection, and generates data to be inspected. The comparator 14 compares the data to be inspected and the reference data generated by the reference data generator 11, and detects defects from the differences. In this case if a plurality of pattern functions having different sensitivity class codes exist in the current inspection region, it references the inspection sensitivities that have been allocated to their sensitivity class codes, and inspects using the smallest inspection sensitivity threshold to detect defects.

The reference data extractor 15 extracts from the reference data the area that corresponds to the location wherein exists the defect that was detected by the comparator 14. In the extracted region of the reference data, the defect registration determinator 16 determines to which pattern function the defect belongs. It then references both the sensitivity class code for the pattern function and the inspection sensitivity that has been allocated to it, and determines whether to register the defect as a real defect. For example, it will register a defect that is greater than or equal to the inspection sensitivity threshold and will not register one that is less. If a defect covers a plurality of pattern functions that have different sensitivity class codes, the pattern function having the highest inspection sensitivity will have priority. Details are described later. The defect memory 17 records a defect for which registration has been determined.

The operation of the inspection device 10 is as follows. When design data corresponding to the subject 20 that is to be inspected is input to the reference data generator 11, it generates reference data to which it appends a sensitivity class code for each design data pattern function. Next, it allocates an inspection sensitivity to each sensitivity class code with the inspection sensitivity setter 12. The actual pattern image of the subject 20 of the inspection is input, as the data to be inspected, into the inspection device 10 by the image acquiring unit 13. The input data is compared with the reference data by the comparator 14 to determine whether a defect exists. At this point, if a defect is detected, the reference data extractor 15 extracts the region in the reference data that corresponds to the defect location. In the extracted region of the reference data, with the defect registration determinator 16 it determines to which pattern function the defect belongs. It then references both the sensitivity class code for the pattern function and the inspection sensitivity that is allocated to it, and determines whether to register the defect as a true defect that must be repaired. The defect for which registration has been determined is stored in the defect memory 17.

Figure 2:
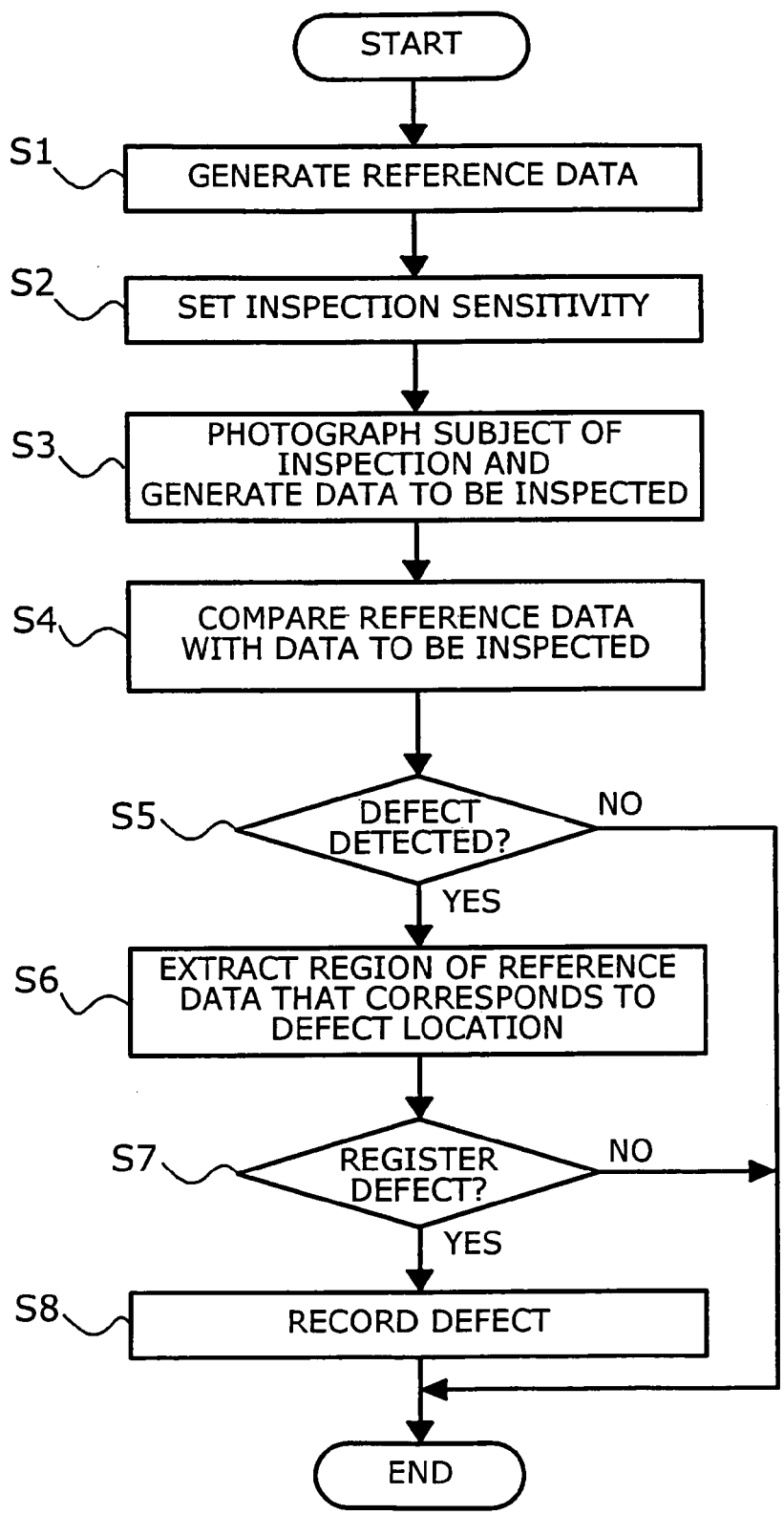
FIG. 2 is a flow chart that shows the concept of an inspection method according to the present invention.

FIG. 2 is a flow chart that shows the concept of an inspection method of the present invention. The method proceeds according to the following steps:

S1: Generate Reference Data

The reference data generator 11 generates reference data that is based on design data and to which it appends a sensitivity class code for each pattern function.

S2: Set Inspection Sensitivity

The inspection sensitivity setter 12 allocates a desired inspection sensitivity to each sensitivity class code in the reference data.

S3: Photograph Subject of Inspection and Generate Data to be Inspected

The image acquiring unit 13 photographs the subject of inspection, and generates data to be inspected.

S4: Compare Reference Data with Data to Be Inspected

The comparator 14 compares the reference data and the data to be inspected, and detects defects from the differences.

S5: Determine Whether a Defect Has Been Detected

If in Step S4 a defect is detected during the comparison, the process proceeds to Step S6. If no defect is detected, the process is terminated.

S6: Extract Region in Reference Data that Corresponds to Defect Location

The reference data extractor 15 extracts the region in the reference data that corresponds to the location of the defect detected by the comparator 14.

S7: Determine Whether to Register the Defect

In the region extracted in Step S6, the defect registration determinator 16 determines to which pattern function the defect belongs. Then it references both the sensitivity class code for the pattern function and the inspection sensitivity that is allocated to it, and determines whether to register the defect as a real defect. If the decision is to register the defect, the process proceeds to Step 8; if it is to not register, the process is terminated.

S8: Record Defect

The defect for which registration has been determined in Step S7 is stored in the defect memory 17.

According to the above, it is possible to differentiate pattern functions by providing a sensitivity class code for each pattern function in the reference data. It is also possible to limit the registration of defects that do not affect performance by setting desired inspection sensitivities for the sensitivity class codes and making the defect registration decision based on the inspection sensitivities. Doing this eliminates the time needed to repair defects that do not affect performance, which makes it possible to reduce the total time from inspection to repair.

Following is a detailed description of an embodiment of an inspection device and method according to the invention.

Figure 3:
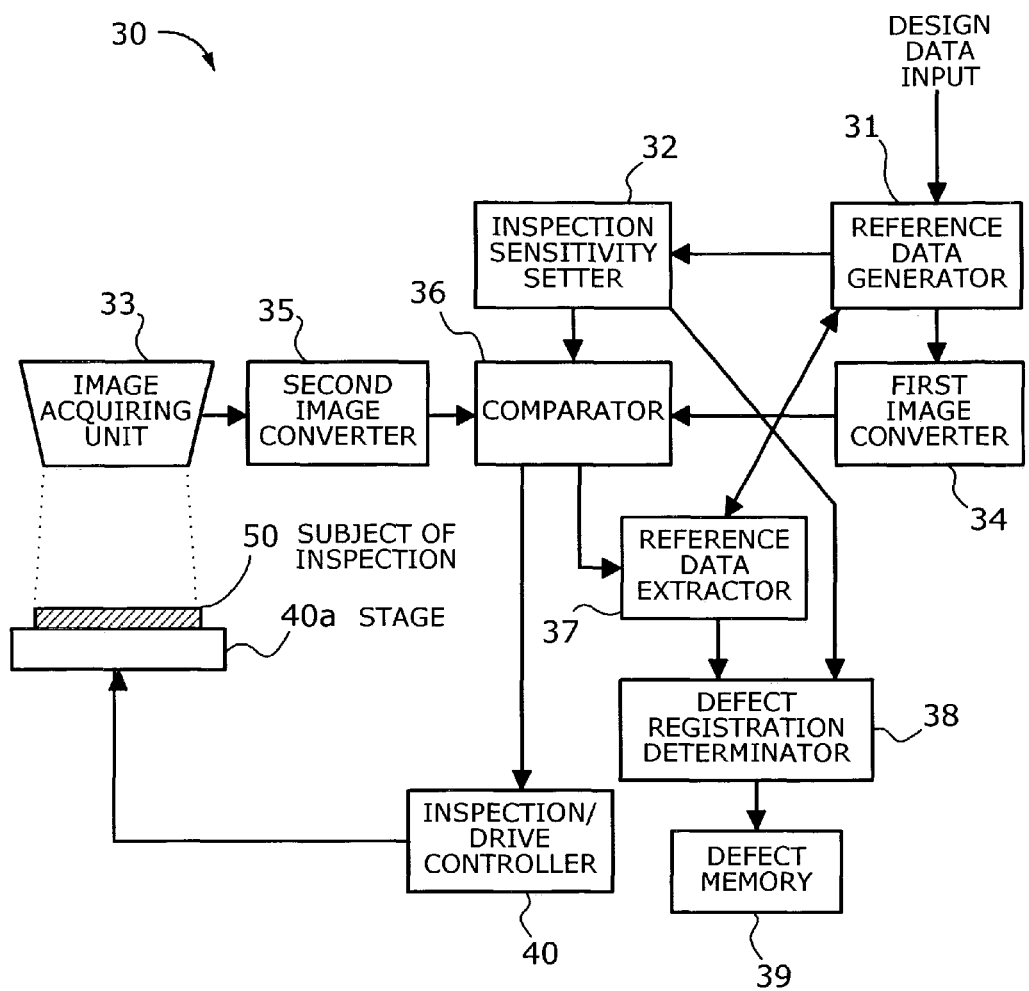
FIG. 3 is a block diagram that shows an embodiment of an inspection device according to the invention.

FIG. 3 is a block diagram that shows an embodiment of an inspection device according to the invention. The inspection device 30 is made up of: (a) a reference data generator 31 that generates reference data that is based on design data and includes sensitivity class codes that are used to differentiate designated pattern functions by means of inspection sensitivity; (b) an inspection sensitivity setter 32 that allocates user-input inspection sensitivities for sensitivity class codes; (c) an image acquiring unit 33 that photographs a subject 50 of the inspection, and generates data to be inspected; (d) a first image converter 34 that converts the reference data into an image; (e) a second image converter 35 that converts the data to be inspected into an image; (f) a comparator 36 that compares the image processed data to be inspected and reference data, and detects a defect; (g) a reference data extractor 37 that extracts a part of the reference data that corresponds to where the detected defect exists (called "reference data block" below); (h) a defect registration determinator 38 that refers to the sensitivity class codes in the reference data block and determines whether to register a defect; (i) a defect memory 39 that records the defect; and (j) an inspection/drive controller 40 that drives a stage 40a on which the subject 50 is to be mounted, and controls all of the inspection device 30.

The reference data generator 31 generates reference data that includes sensitivity class codes that are used to differentiate designated pattern functions by means of inspection sensitivity. Pattern function types include, among others, clock signal lines, address signal lines, data input-output signal lines, control signal lines, and power supply lines. It appends sensitivity class codes to these data by means of characters, numbers, symbols, or other forms. The reference data format will be described later.

The inspection sensitivity setter 32 allocates the desired inspection sensitivity to each sensitivity class code. In this case it is preferred to allocate the highest inspection sensitivity to the clock signal lines, the lowest inspection sensitivity to the power supply lines, and some appropriate inspection sensitivity level equally to the other signal lines. For example, the inspection sensitivity setter 32 gives an inspection threshold value of 1 µm to sensitivity class code "2" for inspection of power lines, and a smaller threshold value of 0.5 µm to sensitivity class code "1" for inspection of signal lines. (Note that a smaller threshold value means a higher sensitivity.)

The image acquiring unit 33 photographs the subject 50 (e.g., photomask or patterned wafer) and generates data to be inspected. Here the image acquiring unit 33 is made up of, among other items, a sensor such as a charge-coupled device (CCD) that converts light into an electronic signal and a signal processor that processes the photographed actual pattern as digital data to be inspected (none shown in the diagram). The first and second image converters 34 and 35 have functionality of image conversion as a preprocess for comparison between the actual pattern data and the reference data. They have been omitted from FIG. 1 for simplicity of explanation.

The comparator 36 compares the converted images of the reference data and the data to be inspected and determines whether a defect exists in the subject 50. The reference data extractor 37 extracts a reference data block for the region to which the defect detected by the comparator 36 belongs. The defect registration determinator 38 creates defect determination ranges in the extracted reference data block that are a prescribed amount larger than the features of the pattern functions to which sensitivity class codes have been appended. It then lays them over the regions in which defects have been detected (called "defect pattern areas" below) and makes the defect registration decision according to the inspection sensitivity. The defect memory 39 records the defect that the defect registration determinator 38 decided to register.

The inspection/drive controller 40 controls, among other things, scan control of the stage 40a on which the subject 50 is mounted, and, although control signal lines are not shown in FIG. 3, the entire inspection device 30. The inspection/drive controller 40 has been omitted from FIG. 1 for simplicity of explanation.

A description of the operation of the inspection device 30 follows. Suppose, for example, that design data for a subject 50 to be inspected, such as a photomask or a wafer that is mounted on the stage 40a, is input from a database or other source (not shown in the diagram) to the reference data generator 31 of the inspection device 30. Then, based on the given design data, the reference data generator 31 generates reference data in a format that is appropriate for inspection. In the reference data, for each pattern function in the design data, a sensitivity class code is appended in order to differentiate according to sensitivity levels. The case in which numbers are used for sensitivity class codes will be described below. In this case sensitivity class codes will be called "sensitivity class numbers."

Figure 4:
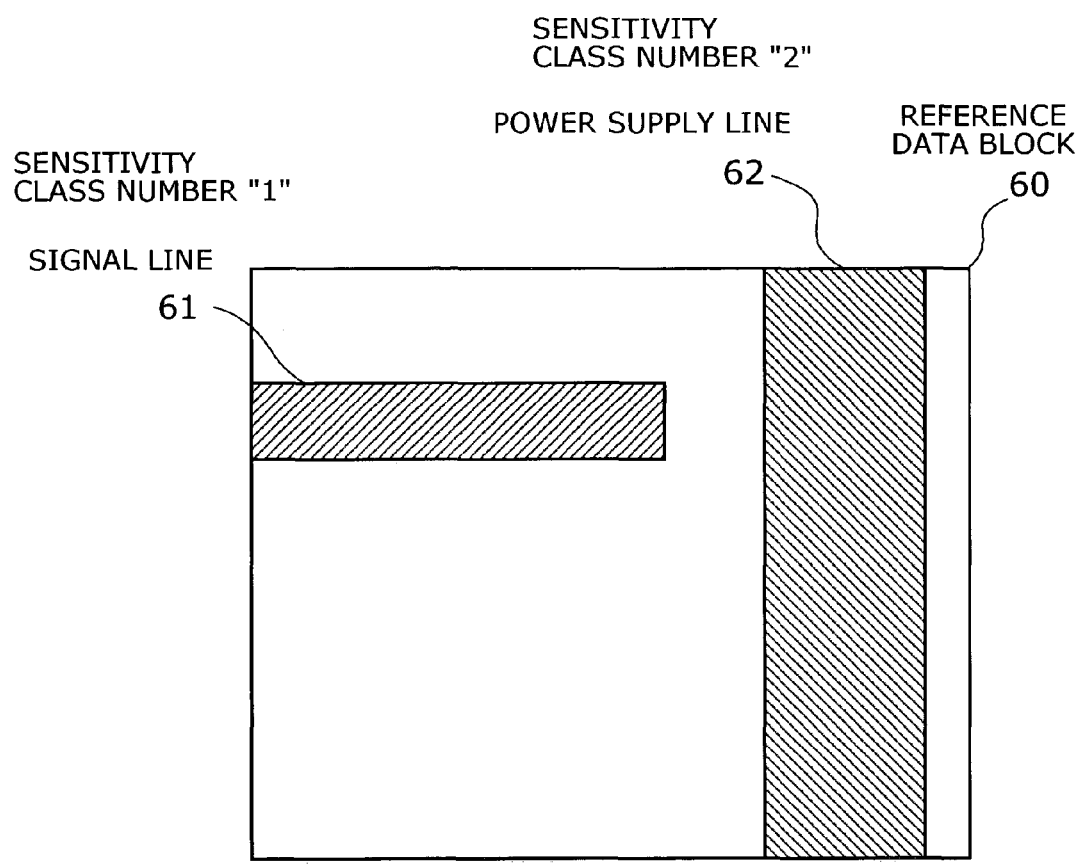
FIG. 4 shows one region of the reference data.

FIG. 4 shows one region of the reference data. Conventional reference data do not differentiate pattern functions. Conversely, for example as in FIG. 4, within the reference data block 60 that is one region of the reference data, the present embodiment of the invention differentiates them from one another by appending sensitivity class number "1" to the signal line 61, and sensitivity class number "2" to the power supply line 62.

Next, the inspection sensitivity setter 32 allocates inspection sensitivities to the sensitivity class numbers that have been appended to each pattern function. For example, when setting inspection conditions, a user could input the inspection sensitivities required for each pattern function. The inspection sensitivity setter 32 will then allocate the input inspection sensitivities to the sensitivity class numbers.

On the other hand, the subject 50 to be inspected is mounted on the stage 40a. Under control of the inspection/drive controller 40, the stage is scanned and the patterns in a designated location on the subject 50 are photographed by the image acquiring unit 33. Then image processing converts them into digital data to be inspected.

Next the first and second image converters 34 and 35 convert respectively the reference data and the data to be inspected into image form, and the comparator 36 compares the resulting image data. When comparing, it references the inspection sensitivities set by the inspection sensitivity setter 32. If, for example as in FIG. 4, pattern functions having differing sensitivity class numbers exist in the reference data block 60, it will detect defects using the smallest inspection threshold.

Figure 5:
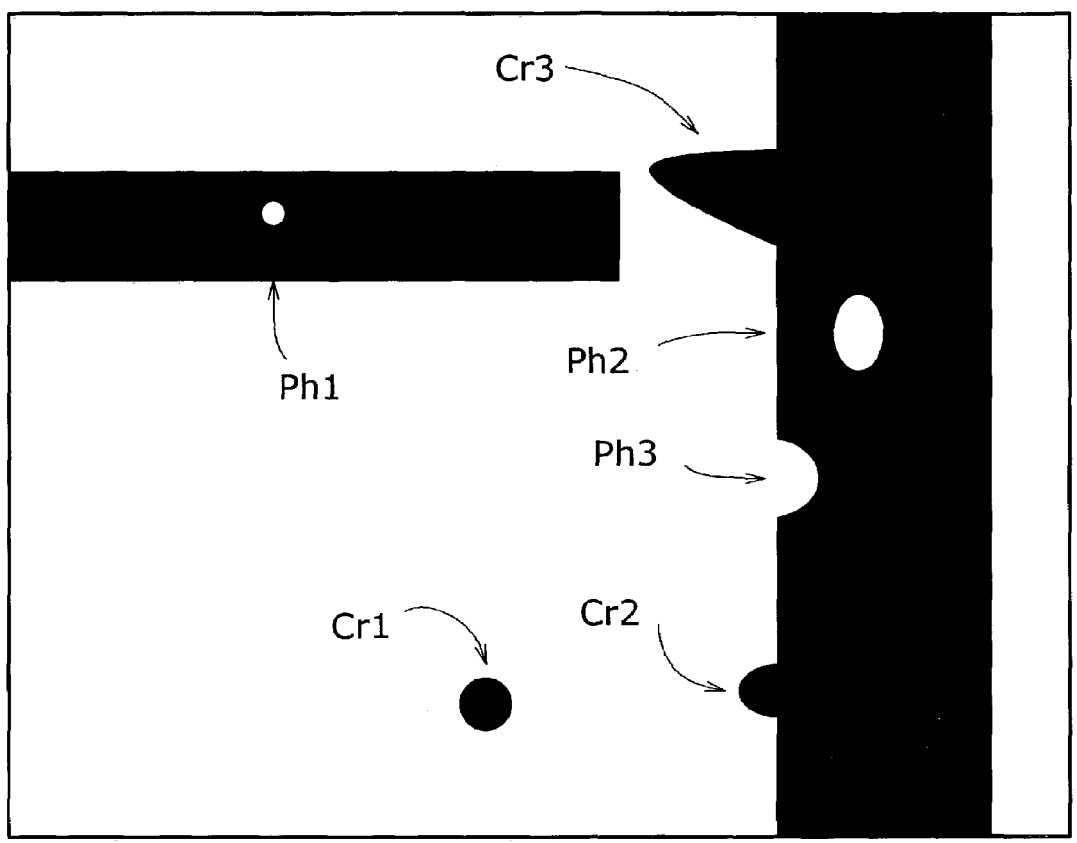
FIG. 5 shows examples of detected defects.

FIG. 5 shows examples of detected defects. This is what the comparator 36 has found on the surface of the subject 50 being inspected (in this case a reticle) in the reference data block 60 shown in FIG. 4. These defects include pinholes Ph1, Ph2, and Ph3 caused by mask sublimation due to lasers or other causes, and a chrome spot Cr1 and chrome extensions Cr2 and Cr3 which are unintended parts of the chrome layer that remain insufficiently etched.

Figure 6:
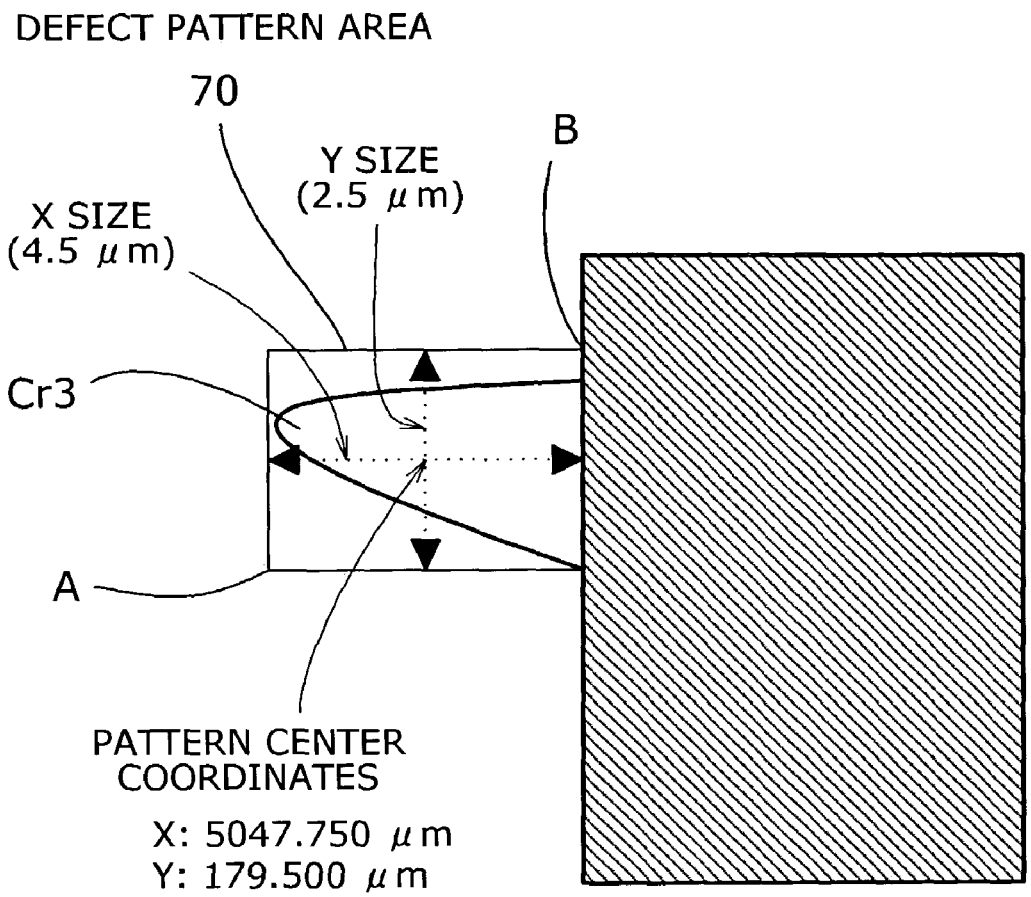
FIG. 6 describes a method of calculating a defect pattern area.

When a defect is detected, the comparator 36 additionally detects the detected defect pattern's central coordinates and the defect's size. It then calculates the defect pattern area. FIG. 6 describes a method of calculating a defect pattern area. This is a description of the method of calculating the defect pattern area for the chrome extension Cr3 shown in FIG. 5. When a defect is detected, its size and central coordinates are measured in the X-Y coordinate system. In the example of FIG. 6, values that include the following are calculated: the X size, which is the length in the X direction, is 4.5 µm, the Y size, which is the length in the Y direction, is 2.5 µm, and the pattern's central coordinates are X:5047.750 µm, Y:179.500 µm. From these is calculated the defect pattern area 70 which is formed by the area represented by two diagonal points A and B in FIG. 6.

Figure 7:
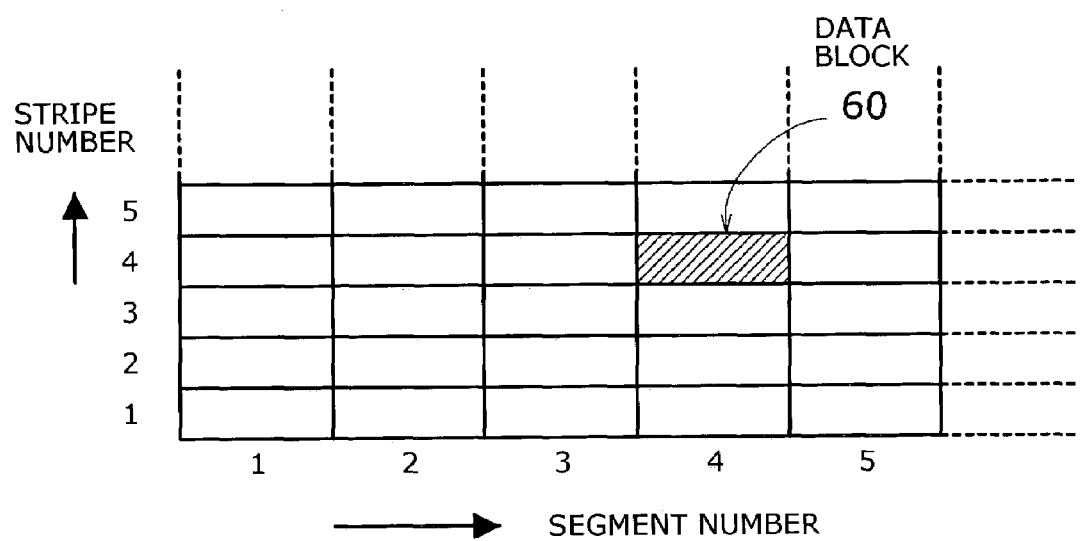
FIG. 7 shows reference data blocks.

Here the reference data format is described. FIG. 7 shows a multiple-block structure for reference data. As the diagram shows, reference data is made of a plurality of data areas, or blocks, shown in the X direction as segment numbers and in the Y direction as stripe numbers. This array of blocks is mapped onto the entire pattern area of the subject 50. Each block contains the geometry definitions of one or more pattern features, together with sensitivity class codes allocated for individual pattern functions.

The reference data extractor 37 extracts from the reference data shown in FIG. 7, for example, the block which contains the defect pattern area 70 that is shown in FIG. 6. Because the coordinates for A and B in FIG. 6 are calculated from the defect size and the pattern's central coordinates, by dividing them by the reference data's stripe and segment unit lengths, it is possible to calculate the location of a data block in the reference data that contains the defect pattern area 70. At this point the calculated reference data block is extracted. For example, in the case that the defect pattern area 70 of chrome extension defect Cr3 shown in FIG. 6 has turned out to belong to the data block at segment 4, stripe 4, the reference data block 60 in FIG. 7 will be extracted.

Figure 8:
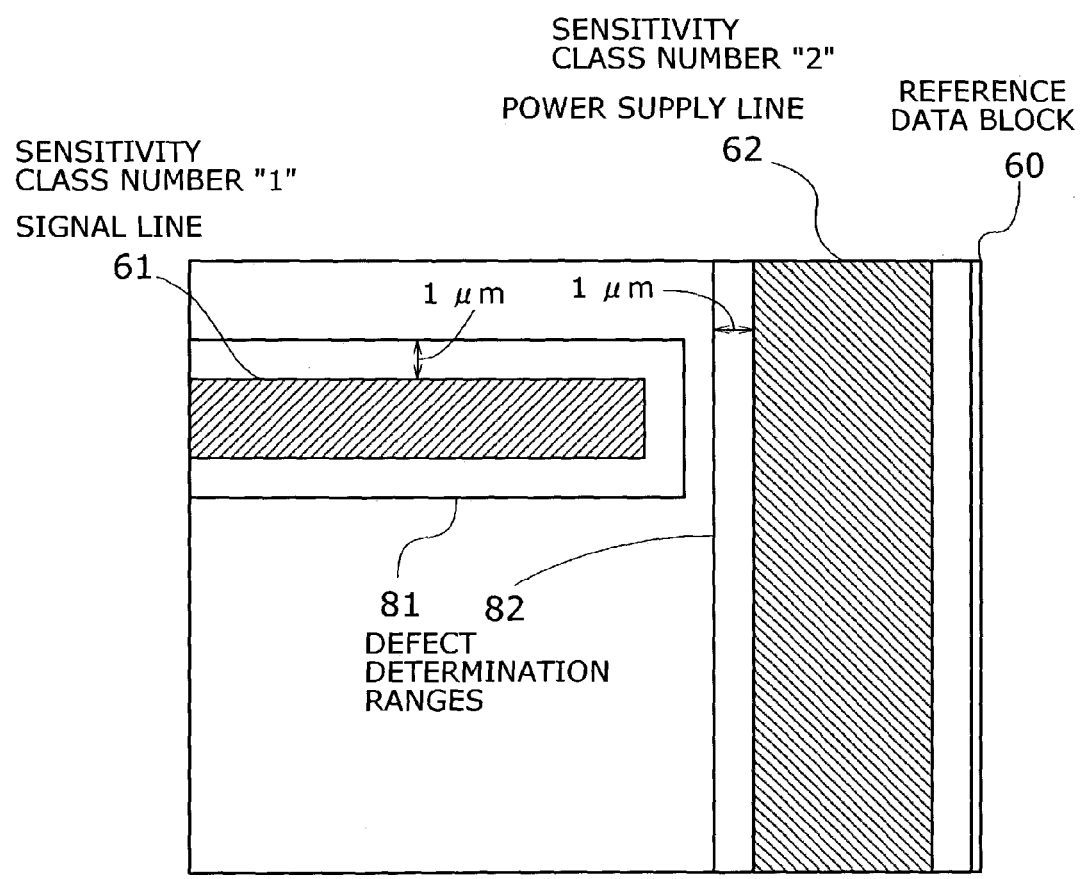
FIG. 8 describes a method of creating defect determination ranges.

Next the operation of the defect registration determinator 38 will be described. First, based on the reference data block 60 that was extracted by the reference data extractor 37, the defect registration determinator 38 creates defect determination ranges. FIG. 8 describes a method of creating defect determination ranges. Defect determination ranges are created in the extracted reference data block 60 by a shift process of a designated amount that is performed on the features of pattern functions that have been differentiated with sensitivity class numbers. FIG. 8 shows pattern functions on which a 1-µm shift has been performed. As can be seen from this diagram, the shift operation displaces the outline of each pattern feature in all outward directions, thereby creating expanded regions. Defect determination ranges 81 and 82 are formed respectively for sensitivity class number "1," signal line 61, and for sensitivity class number "2," power supply line 62.

Figure 9:
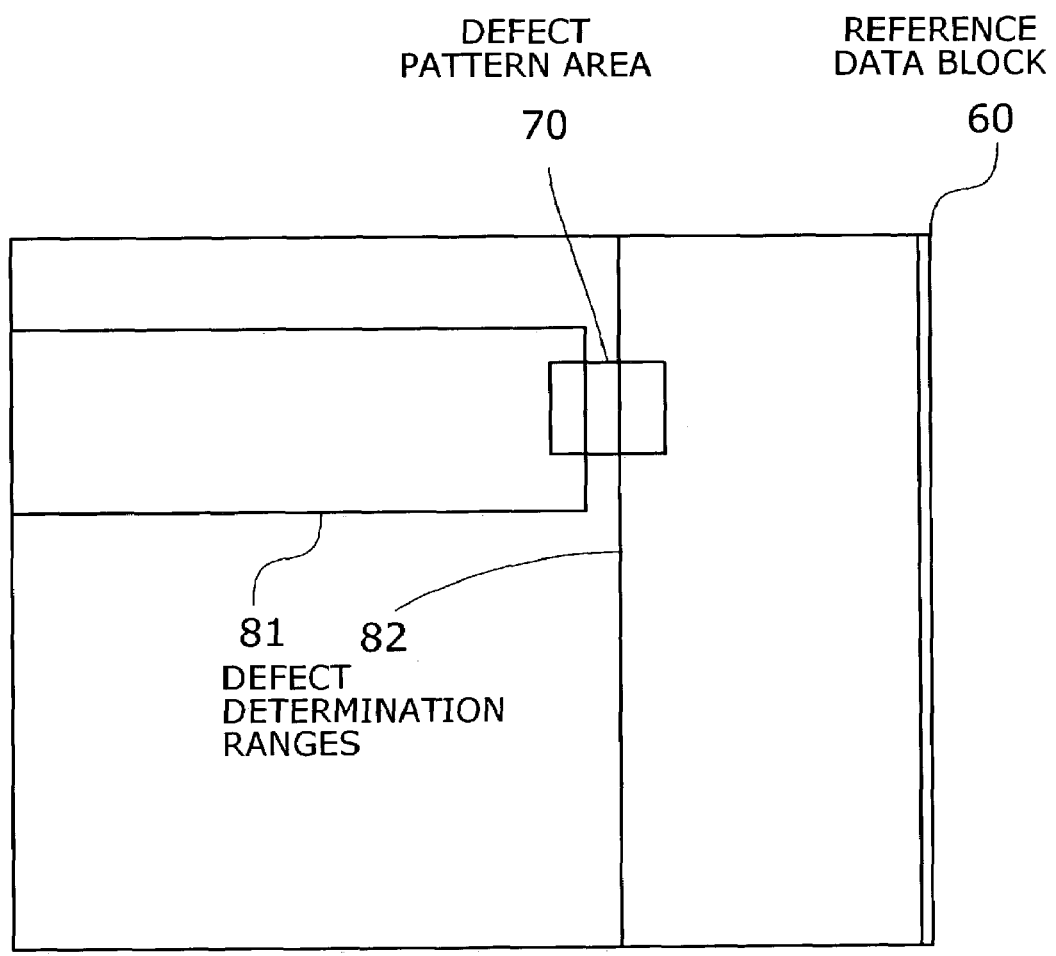
FIG. 9 shows a combination of defect determination ranges and a defect pattern area.

Next the defect pattern area 70 as determined in FIG. 6 is combined with defect determination ranges 81 and 82. FIG. 9 shows a combination of defect determination ranges and a defect pattern area, particularly the case in which the defect pattern area 70 overlaps both of the defect determination ranges 81 and 82. During defect discrimination, a logical AND process is used to find the areas where the defect determination ranges 81 and 82 and the defect pattern area 70 overlap. Defect determination range 81, which corresponds to sensitivity class number "1" that has a higher inspection sensitivity, has priority and is AND processed with the defect pattern area 70. If the result is "1" (i.e., overlap is present), the defect represented by the defect pattern area 70 is registered as a defect that belongs to the defect determination range that corresponds to sensitivity class number "1."

While in FIG. 9 the defect pattern area 70 overlaps both of the defect determination ranges 80 and 81, this is not always the case. If it did not overlap defect determination range 81 (that is, if the above AND process result was "0"), another cycle of logical AND process would then be performed on the next defect determination range 82 and the defect pattern area 70. Here, if the result is "1," the defect represented by the defect pattern area 70 will be determined to belong to the defect determination range 82, which corresponds to sensitivity class number "2." In this case, the inspection sensitivity allocated to sensitivity class number "2" will be referenced, instead of the one allocated to sensitivity class number "1," and if the defect size is smaller than the inspection sensitivity threshold, the defect will not be registered.

Figure 10:
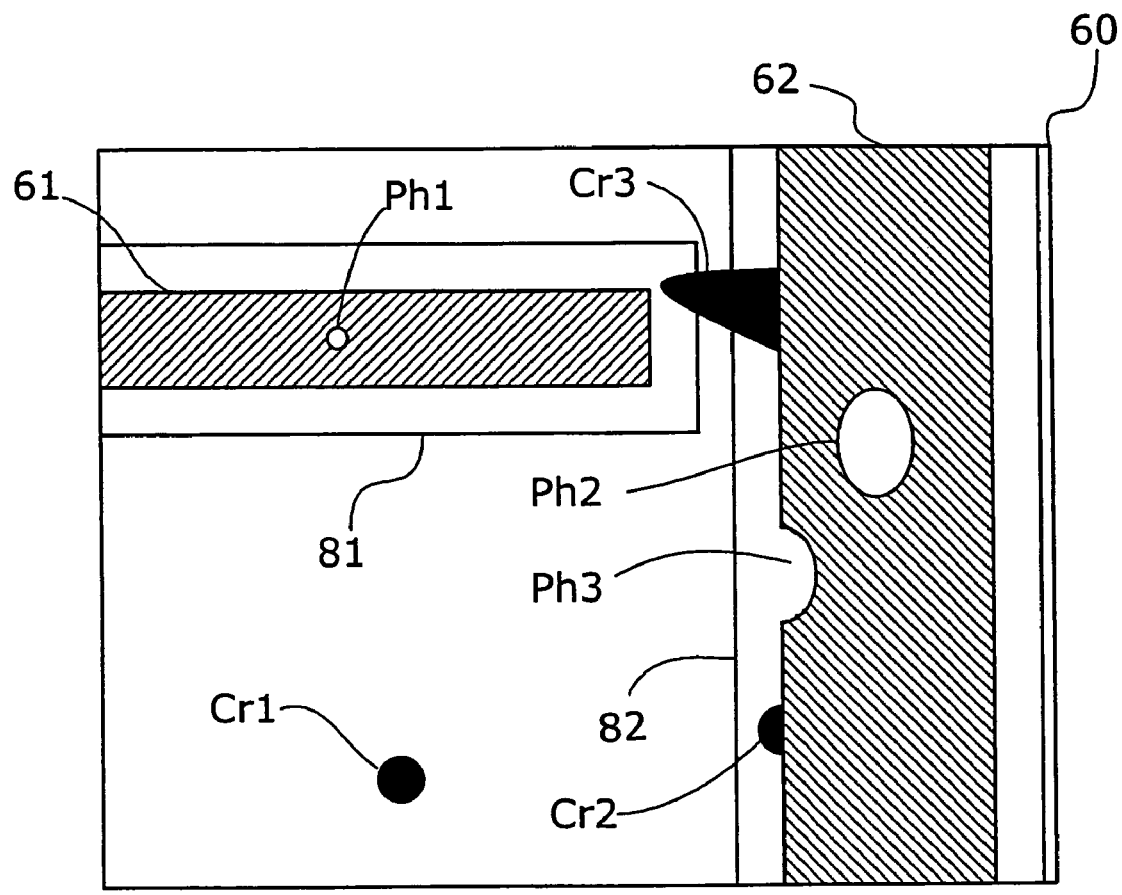
FIG. 10 shows a combination of the defects shown in FIG. 5 and the defect determination ranges and pattern functions shown in FIG. 8.

Defect discrimination for all defects in FIG. 5 will be described below. FIG. 10 shows a combination of the defects shown in FIG. 5 and the defect determination ranges and pattern functions shown in FIG. 8. Here we will assume the following sizes: pinholes Ph1, 0.5 µm; Ph2, 0.8 µm; Ph3, 1.0 µm; chrome spots and extensions Cr1, 1.0 µm; Cr2, 0.9 µm; Cr3 4.5 µm. Additionally the description will be based on sensitivity class number "1" having an inspection sensitivity of 0.5 µm, and sensitivity class number "2" having one of 1.0 µm.

The defect pinhole Ph1 is only associated with defect determination range 81, whose sensitivity class number is "1." Because the defect size is 0.5 µm, which is at least as large as the inspection sensitivity threshold that is allocated to the range 81's sensitivity class number "1," it will be registered as a defect.

The defect pinhole Ph2 is only associated with defect determination range 82, whose sensitivity class number is "2." However, because the defect size is 0.8 μm, which is smaller than the inspection sensitivity threshold of 1.0 μm that is allocated to sensitivity class number "2," it will be not registered as a defect.

The defect pinhole Ph3 is only associated with defect determination range 82, whose sensitivity class number is "2." Because the defect size is 1.0 μm, which is at least as large as the inspection sensitivity threshold that is allocated to sensitivity class number 2, it will be registered as a defect.

On the other hand, because the defect chrome spot Cr1 is not associated with either defect determination range 81 or 82, it will not be registered as a defect.

The defect chrome extension Cr2 is only associated with defect determination range 82, whose sensitivity class number is "2." However, because the defect size is 0.9 μm, which is smaller than the inspection sensitivity threshold of 1.0 μm that is allocated to sensitivity class number "2," it will not be registered as a defect.

The defect chrome extension Cr3 has been described previously. It is associated with both defect determination ranges 81 and 82, which have different sensitivity class numbers "1" and "2," respectively. In this case, priority will be given to sensitivity class number "1," which has the higher inspection sensitivity (i.e., 0.5 μm), and therefore, the chrome extension Cr3 will be registered as a defect.

In the description above, defects that were not associated with defect determination ranges 81 or 82 were not registered as defects. However, a sensitivity class number can also be appended to non-pattern function areas, and an inspection sensitivity value can be allocated to it. In that case, for example, if chrome spot Cr1 was at least as large as the allocated inspection sensitivity value, it would be registered as a defect.

Defects determined to be defects by the defect registration determinator 38 in the manner described above will be recorded in the defect memory 39.

Figure 11:
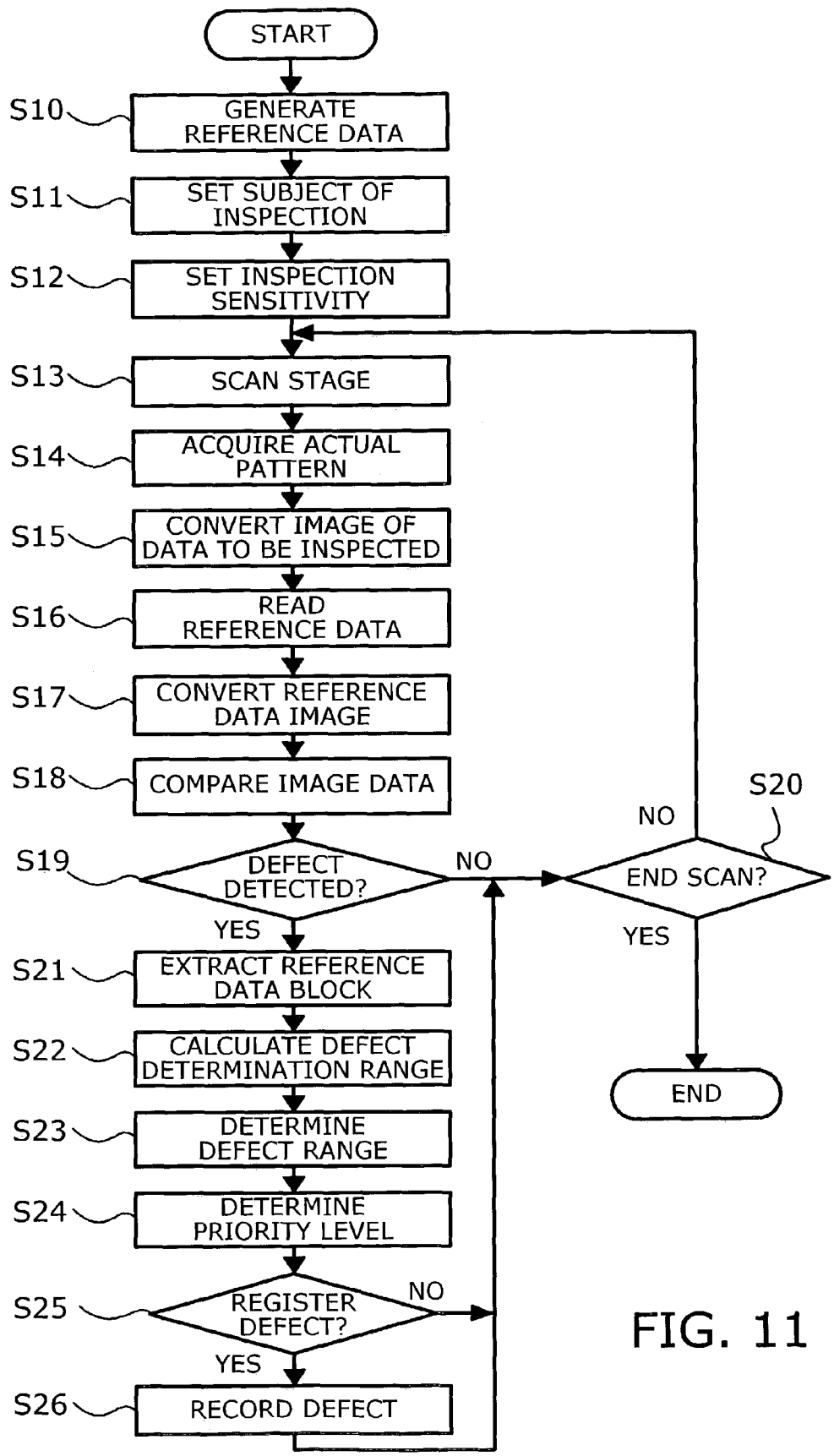
FIG. 11 is a flowchart that shows an inspection method according to an embodiment of the present invention.
Figure 12:
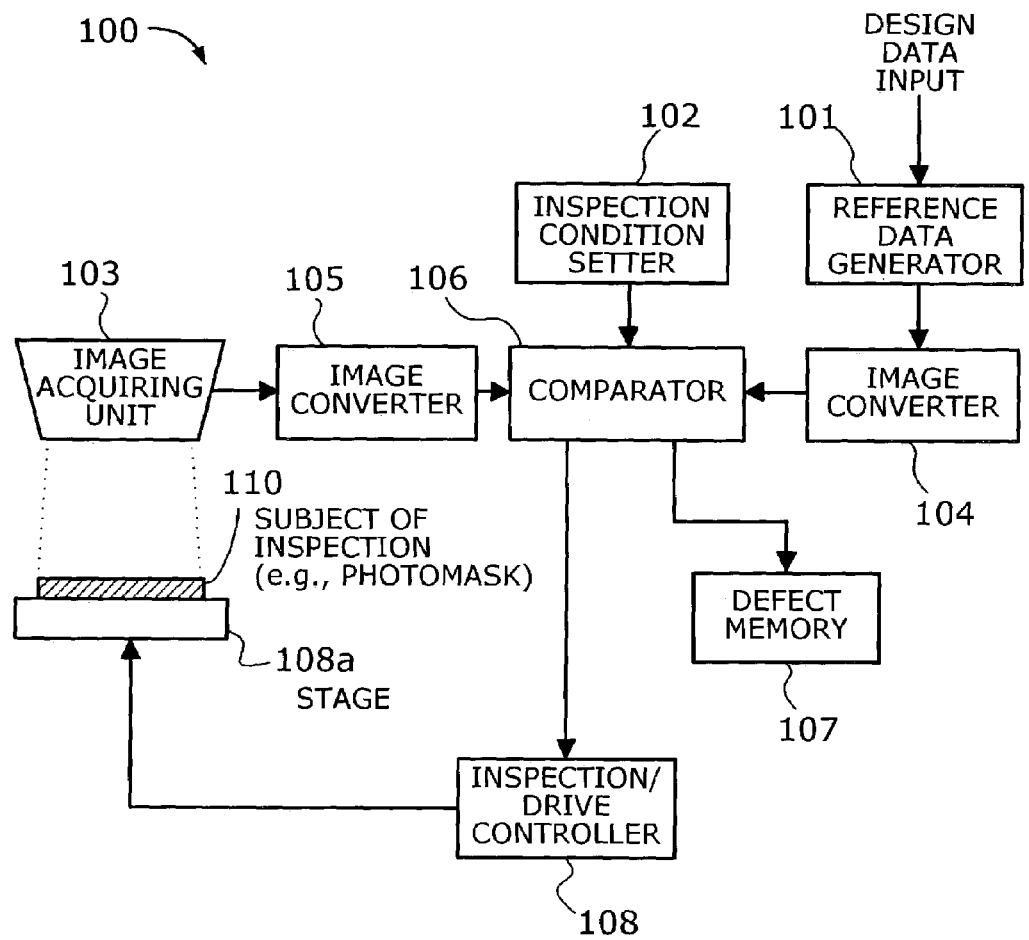
FIG. 12 is a block diagram that shows a conventional inspection device.

Next an inspection method for the previously described inspection device 30 will be described using the flowchart of FIG. 11. The method proceeds according to the following steps:

S10: Generate Reference Data

For each pattern function in the design data generate reference data that includes a sensitivity class code that is used to differentiate by means of inspection sensitivity.

S11: Set Subject of Inspection

The subject 50 of the inspection that could be a photomask, wafer, or other object is set on the stage 40a of the inspection device 30.

S12: Set Inspection Sensitivity

Desired inspection sensitivities are allocated to the sensitivity class codes.

S13: Scan Stage

The stage 40a is driven under control of the inspection/drive controller 40, and the inspection begins from a designated location on the subject 50.

S14: Acquire Actual Pattern

The image acquiring unit 33 acquires, as an image, the actual pattern of the subject 50. The acquired image is converted to digital form, thereby generating the data to be inspected.

S15: Convert Image of Data to Be Inspected

The image of the data to be inspected is converted to enable image data comparison with the reference data.

S16: Read Reference Data

A part of the reference data that corresponds to the acquired actual pattern is read out.

S17: Convert Reference Data Image

The reference data image is converted to enable image data comparison with the data to be inspected.

S18: Compare Image Data

The comparator 36 compares the reference data and the data to be inspected. During the comparison it references the inspection sensitivity settings that were set in Step S12. If, as in FIG. 4, pattern functions having a plurality of differing sensitivity class numbers exist in the current inspection region of the reference data, defect detection will be performed using the smallest inspection sensitivity threshold.

S19: Determine Whether Defect Has Been Detected

The result of the image data comparison in Step S18 is examined. If no defects have been detected, the method proceeds to Step S20. If it is determined that any defects have been detected, the method proceeds to Step S21.

S20: Determine Whether to Terminate Scanning

The inspection/drive controller 40 determines whether the stage scan of the subject 50 has been completed. If it is determined that the scan has been completed, the inspection of the subject 50 will be deemed complete, and processing will terminate. If the scan has not been completed, the process returns to Step S13.

S21: Extract Reference Data Block

Extract a data block that contains a defect pattern area, like the area 70 that is shown in FIG. 6, from reference data like that shown in FIG. 7.

S22: Calculate Defect Determination Range

As shown in FIG. 8, a shift process is performed on the features of the pattern functions that are differentiated by sensitivity class codes, thereby creating defect determination ranges.

S23: Determine Defect Range

As shown in FIG. 9, for example, the defect pattern area 70 is combined with the defect determination ranges 81 and 82. Then it is determined whether the defect pattern area 70 belongs to defect determination range 81 or 82.

S24: Determine Priority Level

If for example, as shown in FIG. 9, the defect pattern area 70 belongs to a plurality of defect determination ranges 81 and 82, priority is determined by referencing the inspection sensitivities that are allocated to the pattern functions' sensitivity class codes.

S25: Determine Whether to Register the Defect

Select either of the defect determination ranges 81 and 82 depending on the priority level obtained in Step S24. With reference to the inspection sensitivity that is allocated to that sensitivity class code, it is determined whether to register the defect. If a defect is to be registered, the method proceeds to Step S26; if none is to be registered, it returns to Step S20.

S26: Record Defect

According to the decision made in Step S25, the detected defect is recorded in the defect memory 39. The process then returns to Step S20.

In this manner it is possible to perform inspections using inspection sensitivities that correspond to pattern functions. This is done by appending sensitivity class codes, which are used to differentiate pattern functions by means of inspection sensitivity, to the reference data, and then allocating inspection sensitivities to the sensitivity class codes.

With the present invention described above, it is possible to differentiate pattern functions by giving sensitivity class code to each pattern function in the reference data. Furthermore, it is possible to reduce the registration of defects that do not affect performance by setting the sensitivity class codes to desired sensitivities and determining the defects to be registered according to those sensitivities. Because it eliminates the time needed to repair defects that do not affect performance, this makes it possible to reduce the overall time from inspection to repair.

The foregoing is considered as illustrative only of the principles of the present invention. Further, since numerous modifications and changes will readily occur to those skilled in the art, it is not desired to limit the invention to the exact construction and applications shown and described, and accordingly, all suitable modifications and equivalents may be regarded as falling within the scope of the invention in the appended claims and their equivalents.

What is claimed is:

1. An inspection device that identifies defects on a subject of inspection including photomasks or products fabricated using photomasks, comprising:
   a reference data generator that generates reference data that is based on design data and includes sensitivity class codes that are used to differentiate designated pattern functions by inspection sensitivity;
   an inspection sensitivity setter that allocates desired inspection sensitivities for said sensitivity class codes;
   an image acquiring unit that detects an image of the subject of the inspection and generates data to be inspected;
   a comparator that compares said data to be inspected with said reference data and detects a defect;
   a reference data extractor that extracts a region of said reference data that corresponds to where said detected defect exists;
   a defect registration determinator that refers to said sensitivity class codes in said region and determines whether to register said defect; and
   a defect memory that records said defect for which registration has been determined,
   the defect registration determinator further:
      determines the detected defect is a non-registration defect if the detected defect is smaller than the inspection sensitivities allocated to the sensitivity class codes, and
      creates a defect determination range by shifting outwardly an outline of a region associated with each of said pattern functions, and based on overlap of said defect and said defect determination range, determines whether to register said defect.

2. The inspection device according to claim 1, wherein said sensitivity class codes are expressed as at least one of a numeral, symbol, and letter.

3. The inspection device according to claim 1, said defect registration determinator further detects which of said pattern functions said defect is associated with based on said overlap, and based on said inspection sensitivity that has been allocated to said detected pattern function, determines whether to register said defect.

4. The inspection device according to claim 1, wherein said sensitivity class codes are set for regions other than those associated with said pattern functions.

5. An inspection method to identify defects on a subject of inspection including photomasks or products fabricated using photomasks, comprising:
   generating reference data that is based on design data and includes sensitivity class codes that are used to differentiate designated pattern functions by inspection sensitivity;
   allocating desired inspection sensitivities for said sensitivity class codes;
   detecting an image of the subject of the inspection and generating data to be inspected;
   comparing said data to be inspected with said reference data and detecting a defect;
   extracting a region of said reference data that corresponds to where said detected defect exists;
   determining whether to register said defect, by referencing the sensitivity class codes of the pattern functions in the extracted region; and
   recording said defect for which registration has been determined,
   the determining further comprising:
      determining the detected defect to be a non-registration defect if the detected defect is smaller than the inspection sensitivities allocated to the sensitivity class codes,
      creating a defect determination range by shifting outwardly an outline of a region associated with each of said pattern functions, and
   based on overlap of said defect and said defect determination range, determining whether to register said defect.

6. The inspection method according to claim 5, wherein said sensitivity class codes are expressed as at least one of a numeral, symbol, and letter.

7. The inspection method according to claim 5, said determining further comprising:
   based on said overlap, detecting which of said pattern functions said defect is associated with; and
   based on said inspection sensitivity that has been allocated to said detected pattern function, determining whether to register said defect.

8. The inspection method according to claim 5, wherein said generating sets sensitivity class codes also for regions other than those associated with said pattern functions.

9. The device according to claim 1, wherein the pattern functions are selected from power supply lines, clock signal lines, address signal lines, data input-output signal lines and control signal lines.

10. The method according to claim 5, wherein the pattern functions are selected from power supply lines, clock signal lines, address signal lines, data input-output signal lines and control signal lines.

11. An inspection method to identify defects, comprising:
   generating sensitivity class codes to differentiate designated pattern functions by inspection sensitivity;
   allocating desired inspection sensitivities for said sensitivity class codes;
   comparing data to be inspected with reference data and detecting a defect; and determining comprising:
whether to register said defect by referencing the sensitivity class codes of the pattern functions,
determining detected defect to be a non-registration defect if the detected defect is smaller than the inspection sensitivities allocated to the sensitivity class codes, creating a defect determination range by shifting outwardly an outline of a region associated with each of said pattern functions, and
based on overlap of said defect and said defect determination range, determining whether to register said defect.

* * * * *

UNITED STATES PATENT AND TRADEMARK OFFICE
CERTIFICATE OF CORRECTION

PATENT NO. : 7,424,145 B2  
APPLICATION NO. : 10/607039  
DATED : September 9, 2008  
INVENTOR(S) : Tsutomu Horie et al.

It is certified that error appears in the above-identified patent and that said Letters Patent is hereby corrected as shown below:

Column 13, line 4, after "determining" insert --the--

Signed and Sealed this

Thirtieth Day of December, 2008

JON W. DUDAS  
*Director of the United States Patent and Trademark Office*